US010499963B2

(12) United States Patent
Paik

(10) Patent No.: US 10,499,963 B2
(45) Date of Patent: *Dec. 10, 2019

(54) FIXING INSTRUMENT FOR OPEN-TYPE DISTAL TIBIAL OSTEOTOMY

(71) Applicant: Hae Sun Paik, Seoul (KR)

(72) Inventor: Hae Sun Paik, Seoul (KR)

( * ) Notice: Subject to any disclaimer, the term of this patent is extended or adjusted under 35 U.S.C. 154(b) by 348 days.

This patent is subject to a terminal disclaimer.

(21) Appl. No.: 15/529,946

(22) PCT Filed: Oct. 28, 2015

(86) PCT No.: PCT/KR2015/011457
§ 371 (c)(1),
(2) Date: May 25, 2017

(87) PCT Pub. No.: WO2016/099028
PCT Pub. Date: Jun. 23, 2016

(65) Prior Publication Data
US 2017/0325858 A1 Nov. 16, 2017

(30) Foreign Application Priority Data
Dec. 16, 2014 (KR) .......... 10-2014-0181539

(51) Int. Cl.
A61B 17/80 (2006.01)
A61B 17/82 (2006.01)
(Continued)

(52) U.S. Cl.
CPC .......... *A61B 17/80* (2013.01); *A61B 17/1728* (2013.01); *A61B 17/8033* (2013.01); *A61B 17/82* (2013.01); *A61B 17/86* (2013.01)

(58) Field of Classification Search
CPC .......................................... A61B 17/80–8095
See application file for complete search history.

(56) References Cited

U.S. PATENT DOCUMENTS 8,246,660 B2 * 8/2012 Boris ................... A61B 17/808
606/246
2003/0199875 A1 * 10/2003 Mingozzi ........... A61B 17/8095
606/297
(Continued)

FOREIGN PATENT DOCUMENTS

EP 1308135 A2 5/2003
FR 2785519 A1 5/2000
(Continued)

OTHER PUBLICATIONS

Extended European Search Report for Application No. 15870196.1, dated Jul. 19, 2018.
(Continued)

Primary Examiner — Zade Coley
(74) Attorney, Agent, or Firm — STIP Law Group, LLC

(57) ABSTRACT

A fixing instrument for an open-type distal tibial osteotomy according to an exemplary embodiment of the present invention is installed on a tibia incised by the open-type distal tibial osteotomy, and the fixing instrument includes: a body portion which is in close contact with the tibia and has a plurality of coupling holes and an oblong hole; a head portion which is connected to one end of the body portion and has a plurality of coupling holes; screws which are inserted into the coupling holes; and a block which is detachably installed in the oblong hole by using a sliding screw, in which the head portion is formed to have a predetermined angle based on a lower surface of the head portion, and the other end of the body portion is formed to have a predetermined angle based on a lower surface of the body portion.

10 Claims, 5 Drawing Sheets

(51) Int. Cl.
*A61B 17/86* (2006.01)
*A61B 17/17* (2006.01)

(56) References Cited

U.S. PATENT DOCUMENTS

| | | | | |
|---|---|---|---|---|
| 2004/0260295 | A1* | 12/2004 | Orbay | A61B 17/68 606/86 B |
| 2005/0107796 | A1* | 5/2005 | Gerlach | A61B 17/8014 606/281 |
| 2005/0234472 | A1* | 10/2005 | Huebner | A61B 17/683 606/104 |
| 2005/0251138 | A1* | 11/2005 | Boris | A61B 17/7071 623/17.11 |
| 2006/0015102 | A1* | 1/2006 | Toullec | A61B 17/8061 606/86 B |
| 2006/0041260 | A1* | 2/2006 | Orbay | A61B 17/8042 606/287 |
| 2007/0239163 | A1* | 10/2007 | Strnad | A61B 17/8047 606/286 |
| 2008/0300637 | A1* | 12/2008 | Austin | A61B 17/74 606/290 |
| 2009/0143825 | A1 | 6/2009 | Graham et al. | |
| 2009/0248084 | A1 | 10/2009 | Hintermann | |
| 2010/0016858 | A1* | 1/2010 | Michel | A61B 17/8057 606/70 |
| 2011/0160730 | A1* | 6/2011 | Schonhardt | A61B 17/8061 606/71 |
| 2011/0264149 | A1* | 10/2011 | Pappalardo | A61B 17/8019 606/286 |
| 2012/0184959 | A1* | 7/2012 | Price | A61B 17/8009 606/70 |
| 2014/0039498 | A1* | 2/2014 | Chatain | A61B 17/8095 606/70 |
| 2015/0335366 | A1* | 11/2015 | Dacosta | A61B 17/8095 606/281 |

FOREIGN PATENT DOCUMENTS

| | | |
|---|---|---|
| JP | 2011-515172 A | 5/2011 |
| KR | 10-2006-0035604 A | 4/2006 |
| KR | 10-2006-0115603 A | 11/2006 |
| KR | 10-2008-0107390 A | 12/2008 |
| KR | 10-1253915 B1 | 4/2013 |

OTHER PUBLICATIONS

International Search Report for International Patent Application No. PCT/KR2015/011457 filed Oct. 28, 2015.

* cited by examiner

FIXING INSTRUMENT FOR OPEN-TYPE DISTAL TIBIAL OSTEOTOMY

CROSS-REFERENCE TO RELATED APPLICATIONS

The present specification is a U.S. National Stage of International Patent Application No. PCT/KR2015/011457 filed Oct. 28, 2015, which claims priority to and the benefit of Korean Patent Application No. 10-2014-0181539, filed Dec. 16, 2014, the entire contents of which are incorporated herein by reference.

TECHNICAL FIELD

The present invention relates to a fixing instrument for an open-type distal tibial osteotomy. More particularly, the present invention relates to a fixing instrument for an open-type distal tibial osteotomy which ensures secure fixing force by bringing a plate into contact with an inner side of an ankle after the open-type distal tibial osteotomy.

BACKGROUND ART

In general, degenerative arthritis may occur in various forms at a joint portion of a human body.

In a case in which degenerative arthritis occurs in an inner ankle or the inner ankle has avascular necrosis, pain of an ankle portion, which supports a load of the human body, is increased, and thus a patient may have difficulty in walking.

In this case, there is an inner ankle osteotomy as one of the recommended surgical methods, and the inner ankle osteotomy is a treatment method which corrects an abnormal axis of the ankle and shifts a load, which is applied to the ankle joint, to a healthy outer joint surface, thereby improving a distribution of stress and a joint arrangement, and thus alleviating pain.

Unlike artificial joint replacement, the inner ankle joint osteotomy is a method capable of preserving the joint and has an advantage in that an artificial joint surgery time may be delayed, and a joint movement range may be maintained to be almost similar to a joint movement range before the surgery.

In most cases, a distal tibial osteotomy, which corrects concentration of a load by cutting a thick bone positioned at an upper side of the inner ankle, is performed, and when performing the distal tibial osteotomy, the bone is cut and then spread by a necessary angle, bone transplantation is performed, and then the bone is fixed by using a plate and screws.

However, the plate in the related art do not match with Korean body types, and angles at an osteotomy site are misaligned, and as a result, there is a problem in that complications are caused after the surgery.

DOCUMENT OF RELATED ART

Korean Patent No. 10-0641312

DISCLOSURE

Technical Problem

An exemplary embodiment of the present invention provides a fixing instrument for an open-type distal tibial osteotomy which is capable of having secure coupling force by rotating a head portion of a plate.

In addition, an exemplary embodiment of the present invention provides a fixing instrument for an open-type distal tibial osteotomy in which a head portion has an angle so that coupling screws are not withdrawn from a bone.

Technical Solution

A fixing instrument for an open-type distal tibial osteotomy according to an exemplary embodiment of the present invention is installed on a tibia incised by the open-type distal tibial osteotomy, and the fixing instrument includes: a body portion which is in close contact with the tibia and has a plurality of coupling holes and an oblong hole; a head portion which is connected to one end of the body portion and has a plurality of coupling holes; screws which are inserted into the coupling holes; and a block which is detachably installed in the oblong hole by using a sliding screw, in which the head portion is formed to have a predetermined angle based on a lower surface of the head portion, and the other end of the body portion is formed to have a predetermined angle based on a lower surface of the body portion.

Particularly, the head portion may be connected to one end of the body portion and formed to be twisted in a left or right direction together with the body portion.

Particularly, the head portion may be formed to be wider in width than the body portion, and the plurality of coupling holes formed in the head portion may be formed such that central portions of the coupling holes are positioned at apices of a triangle.

Particularly, the head portion and the body portion may be formed to be curved and be in close contact with the tibia.

Particularly, one surface of the head portion may have an inclination angle of 24 to 26 degrees based on a bottom surface of the body portion.

Particularly, the other surface of the head portion may have two-stage inclination sections based on the bottom surface of the body portion.

Particularly, the inclination sections may include a first inclined portion and a second inclined portion, and the first inclined portion may have a smaller inclination angle than the second inclined portion.

Particularly, the first inclined portion may form an inclination angle of 15 to 16 degrees based on the bottom surface of the body portion, and the second inclined portion may form an inclination angle of 16 to 17 degrees based on the bottom surface of the body portion.

Particularly, the body portion may have two-stage inclination sections, and the inclination sections may have different left and right inclinations.

Particularly, the body portion may have a first inclination section and a second inclination section, and the first inclination section may have a smaller inclination angle than the second inclination section.

Particularly, at least one guide hole to which a guide pin is fixed may be formed in the head portion or the body portion.

Particularly, a length of the block which is inserted into an incised portion may be 4 to 10 mm, and a height thereof may be one of 3.8 to 4.2 mm, 5.8 to 6.2 mm, 7.8 to 8.2 mm, and 9.8 to 10.2 mm.

Advantageous Effects

According to the fixing instrument for an open-type distal tibial osteotomy according to the exemplary embodiment of the present invention, it is possible to securely couple the plate and the bone by rotating the head portion.

In addition, since angles are formed at the head portion and thus the coupling screws are not withdrawn from the bone, it is possible to reduce complications after the surgery.

In addition, the sliding hole is formed in the body portion, such that the block may be inserted to be suitable for a surgical site.

BEST MODE

Figure 1:
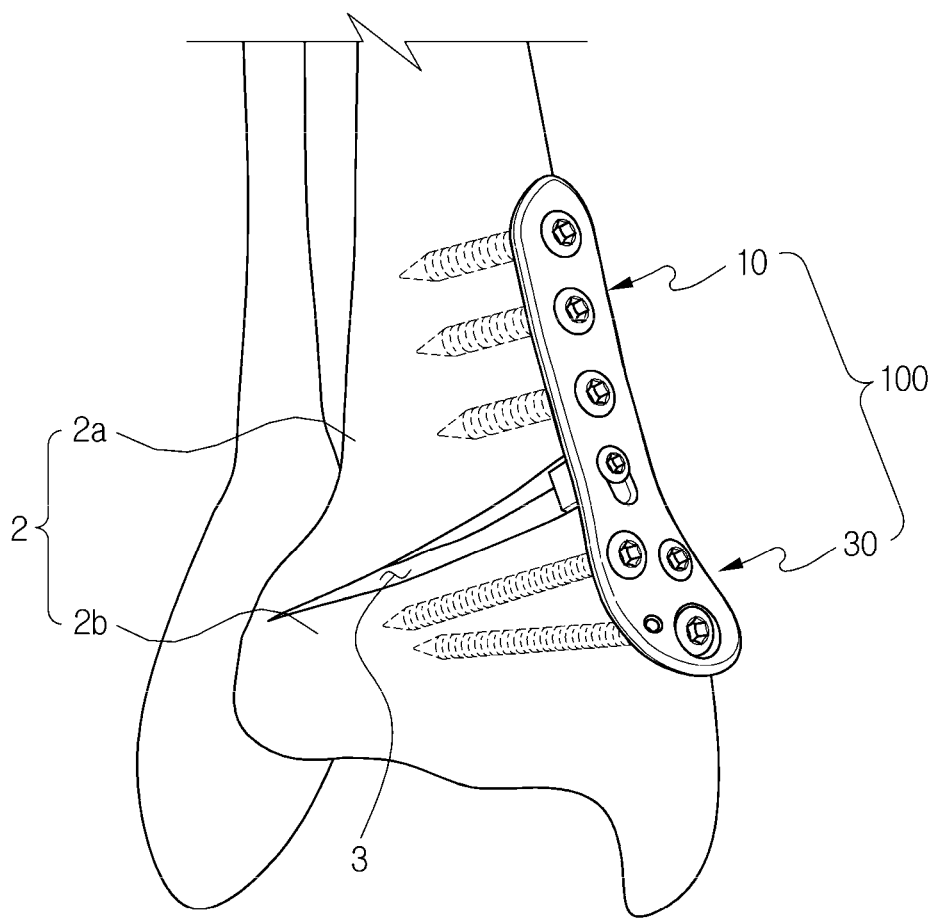
FIG. 1 is a view illustrating a state in which a fixing instrument for an open-type distal tibial osteotomy according to an exemplary embodiment of the present invention is coupled to a tibia.

Hereinafter, a fixing instrument for an open-type distal tibial osteotomy according to an exemplary embodiment of the present invention will be described in detail with reference to the accompanying drawings. First, in denoting reference numerals to constituent elements of the respective drawings, it should be noted that the same constituent elements will be designated by the same reference numerals, if possible, even though the constituent elements are illustrated in different drawings. Further, an exemplary embodiment of the present invention will be described below, but the technical spirit of the present invention is not limited thereto and may be modified and variously carried out by those skilled in the art.

Figure 2:
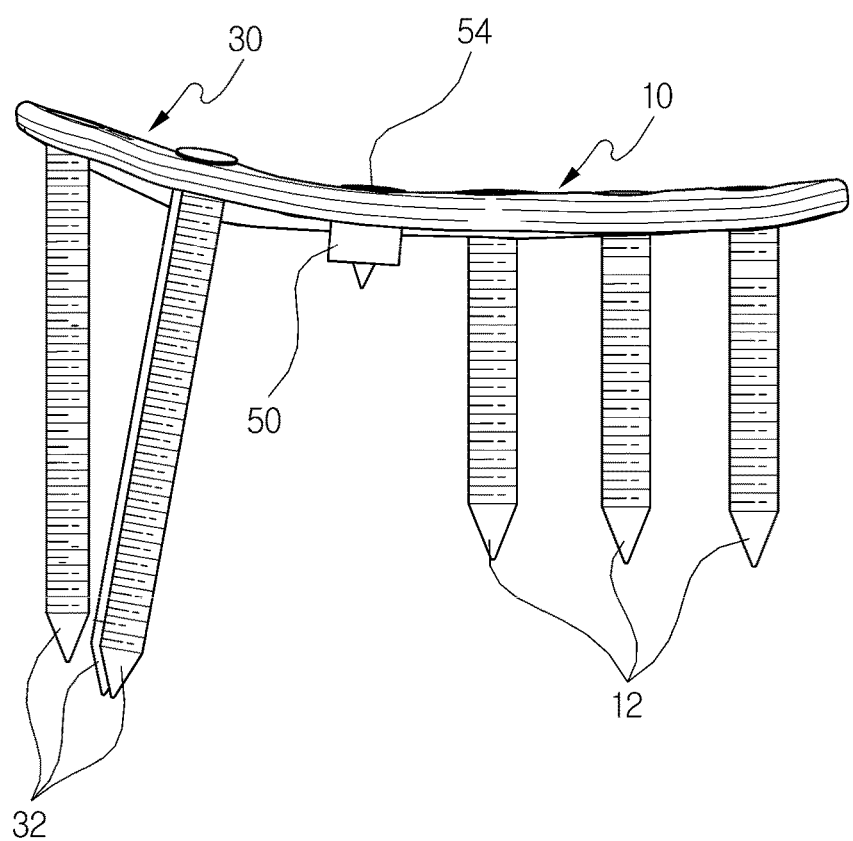
FIG. 2 is a view illustrating the fixing instrument for an open-type distal tibial osteotomy according to the exemplary embodiment of the present invention when viewed from a lateral side.
Figure 3:
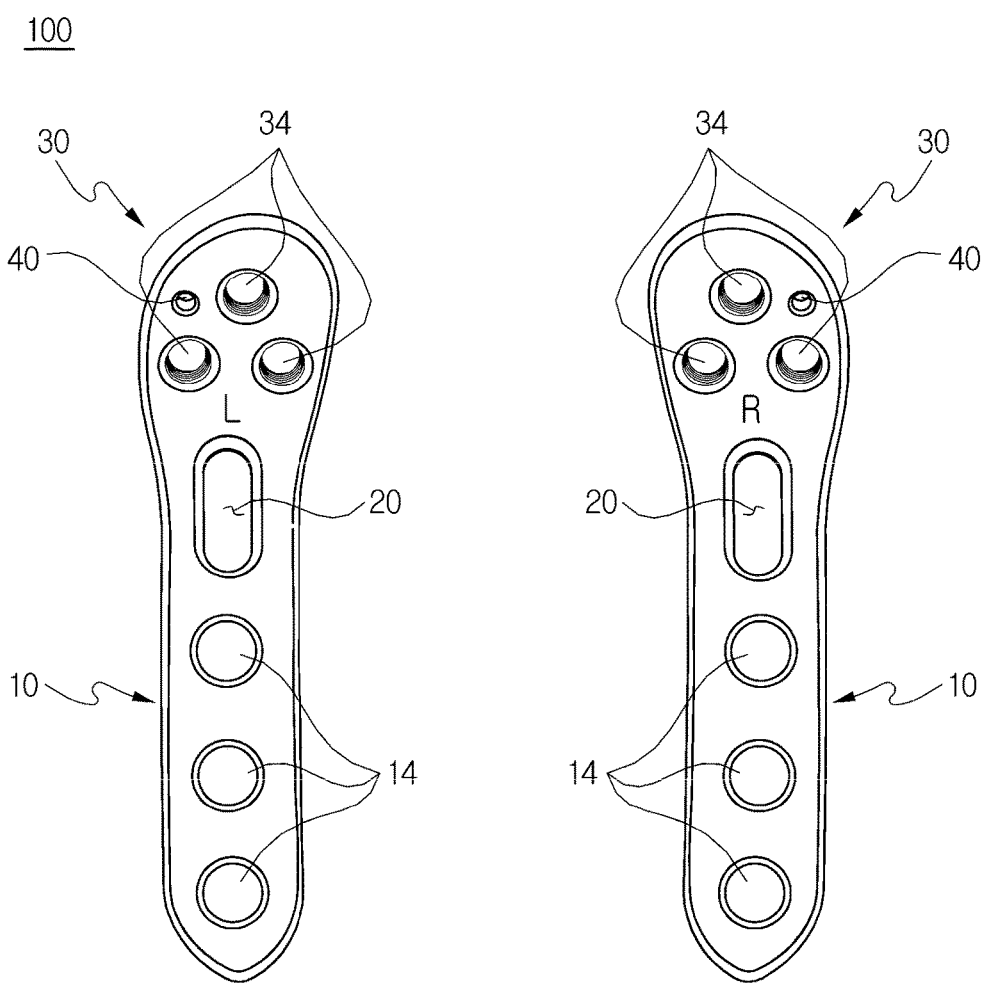
FIG. 3 is a view illustrating a shape of a plate which is a constituent element of the present invention.

FIG. 1 is a view illustrating a state in which a fixing instrument for an open-type distal tibial osteotomy according to an exemplary embodiment of the present invention is coupled to a tibia, FIG. 2 is a view illustrating the fixing instrument for an open-type distal tibial osteotomy according to the exemplary embodiment of the present invention when viewed from a lateral side, and FIG. 3 is a view illustrating a shape of a plate which is a constituent element of the present invention.

A fixing instrument 1 for an open-type distal tibial osteotomy according to an exemplary embodiment of the present invention will be described with reference to FIGS. 1 and 3.

Referring to FIG. 1, a tibia 2 is divided into an upper tibia 2a and a lower tibia 2b based on an incised portion 3 which is incised by a distal tibial osteotomy procedure for incising the tibia 2.

The fixing instrument 1 for an open-type distal tibial osteotomy according to the exemplary embodiment of the present invention may include a body portion 10 which is in close contact with the tibial 2 and has a plurality of coupling holes 14 and an oblong hole 20, a head portion 30 which is connected to one end of the body portion 10 and has a plurality of coupling holes 34, screws 12 and 32 which are inserted into the coupling holes 14 and 34, and a block 50 which is detachably installed in the oblong hole 20 by using a sliding screw 54.

A plate 100 of the fixing instrument 1 for an open-type distal tibial osteotomy according to the exemplary embodiment of the present invention may be classified into a left-hand plate and a right-hand plate in accordance with a surgical site, and the left-hand plate and the right-hand plate define a symmetrical structure.

The plate 100 may include the body portion 10 and the head portion 30, and may have the plurality of coupling holes 14 and 34 into which the screws 12 and 32 for fixing the plate 100 to the tibial 2 are inserted.

The body portion 10 may be formed in an elongated shape, and the plurality of coupling holes 14 may be formed in a longitudinal direction of the body portion 10. One end of the body portion 10 is connected to the head portion 30, and the other end of the body portion 10 is formed to have a predetermined angle based on a lower surface of the body portion 10, such that the body portion 10 may be in close contact with the tibia 2. The plurality of coupling holes 14 formed in the body portion 10 is formed at predetermined intervals so as to uniformly distribute supporting force applied to the plate 100. The screws 12, which penetrate the plurality of coupling holes 14 formed in the body portion 10, may be coupled to the upper tibia 2a at a right angle to the upper tibia 2a. A length of each of the screws 12 coupled to the body portion 10 may be variously modified in accordance with a diameter of the upper tibia 2a. In addition, a diameter of the screw 12 coupled to the body portion 10 may be 4 to 6 mm, particularly, 5 mm.

The block 50 may be connected to the oblong hole 20 formed in the body portion 10 by using the sliding screw 54. The block 50 may be inserted into the incised portion 3 of the tibia 2, thereby supporting the incised portion 3. The sliding screw 54 serves to fix the block 50 to the body portion 10, and a length of the sliding screw 54 is adjusted so that a through portion of the sliding screw 54, which fixes the block 50 to the body portion 10 and penetrates the block 50, does not come into contact with the incised portion 3.

When performing the open-type distal tibial osteotomy, an abnormal axis of an ankle is corrected by incising one surface of the tibia 2, and spreading the incised site. In this case, the incised portion 3, which is formed in the tibia 2 when performing the open-type distal tibial osteotomy, is not always fixed, and thus when the plate 100 is fixed to match with a position of the incised portion 3 in a case in which an insertion position of the block 50 is fixed, the plate 100 does not coincide with a curved surface of the tibia 2, and as a result, there is a problem in that the plate 100 cannot be in close contact with the tibia 2.

To solve the problem, the oblong hole 20 is formed in the body portion 10 in the longitudinal direction, and thus a position of the block 50 may be adjusted in accordance with a position of the incised portion 3 formed during the surgery.

The head portion 30 is connected to one end of the body portion 10, and may be formed to have a predetermined angle in an upward direction based on the lower surface of the head portion 30. The head portion 30, together with the body portion 10, may be twisted in a left or right direction so as to have a predetermined angle.

The head portion 30 may be formed to be wider in width than the body portion 10. The plurality of coupling holes 34 may be formed in the head portion 30, and the screws 32 are inserted into the coupling holes 34, such that the head portion 30 may be coupled to the lower tibia 2b so as to be in close contact with the lower tibia 2b. The coupling holes 34 formed in the head portion 30 may be formed to be positioned at apices of a triangle. The coupling holes 34 may be coupled so that ends of the screws 32 inserted into the coupling holes 34 formed in the head portion 30 are directed toward any one point. The screws 32, which are inserted into the lower tibia 2b and coupled to the head portion 30, are coupled to be directed toward any one point, such that the screws 32 may be coupled to the lower tibia 2b without penetrating a joint surface or the incised portion 3.

As an exemplary embodiment, the screw 32, which is coupled to the coupling hole 34 formed at an uppermost end of the head portion 30 among the coupling holes 34 positioned at the apices of the triangle, is coupled to the tibia 2 in a vertical direction, and the screws 32, which are coupled to the remaining two apices, are coupled to be inclined so as to be directed toward any one point.

The coupling shape of the screws 12 and 32 coupled to the head portion 30 may be variously modified to a coupling shape in which the screws 12 and 32 do not penetrate the lower tibia 2b.

The screw 32 inserted into the head portion 30 may be formed to have a diameter of 3 to 4 mm, particularly, 3.5 mm.

The body portion 10 and the head portion 30, which are constituent elements of the plate 100, are divided as necessary, but the body portion 10 and the head portion 30 may be integrally formed. At least one guide hole to which a guide pin (not illustrated) is fixed may be formed in the plate 100. The plate 100 may be temporarily fixed by installing the guide pin (not illustrated) into the guide hole 40 before inserting the screws 12 and 32.

The reason is to prevent the plate 100 from moving when the screws 12 and 32 are inserted into the coupling holes 14 and 34 formed in the plate 100. The guide pin (not illustrated) is removed after the plate 100 is in close contact with the tibia 2.

As an exemplary embodiment, at least one guide hole 40 may be formed in the head portion 30 in order to fix the head portion 30. A plurality of positions of the guide holes 40 may be formed to fix the plate 100, and the positions of the guide holes 40 for fixing the plate 100 may be modified to various positions.

Figure 4:
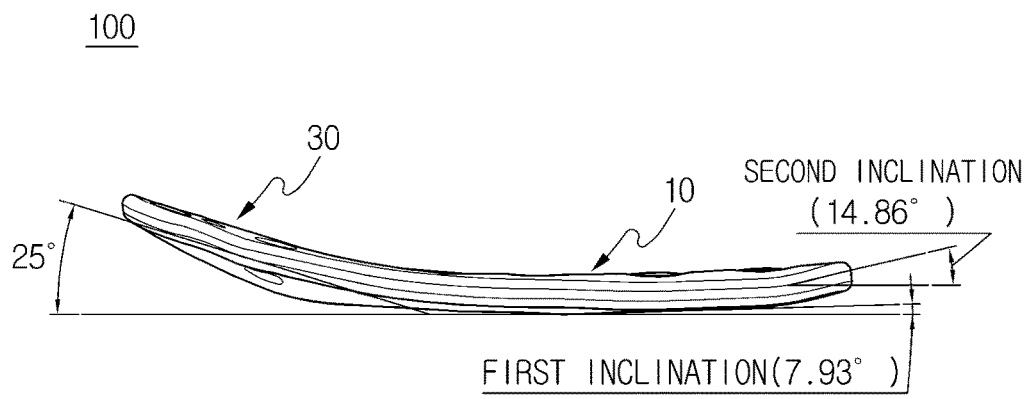
FIG. 4 is a view illustrating the plate in FIG. 3 when viewed from one side.
Figure 5:
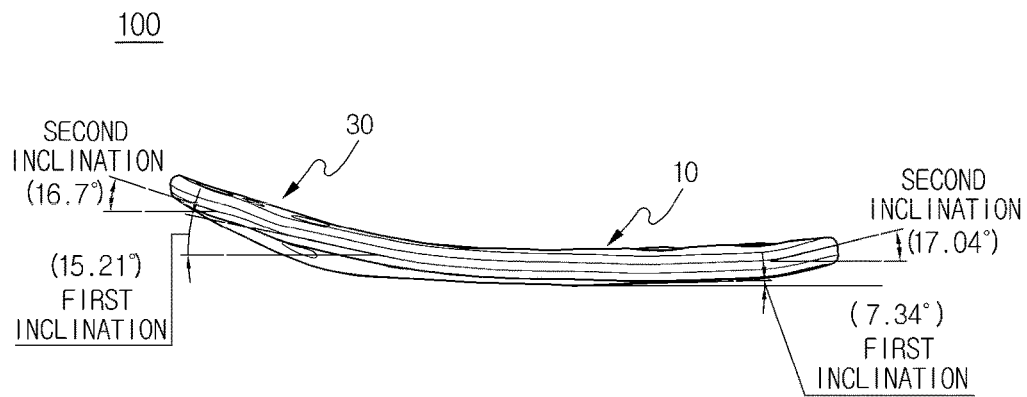
FIG. 5 is a view illustrating the plate in FIG. 3 when viewed from the other side.

FIG. 4 is a view illustrating the plate, which is a constituent element of the present invention, when viewed from one side, and FIG. 5 is a view illustrating the plate, which is a constituent element of the present invention, when viewed from the other side.

Referring to FIGS. 4 and 5, the head portion 30 of the plate 100 is connected to one end of the body portion 10 and is inclined in the upward direction, and the other end of the body portion 10 may be inclined in the upward direction based on the body portion 10. In addition, the plate 100 may be entirely twisted in the left or right direction. The reason is to bring the plate 100 into close contact with the tibia 2 by means of an anatomical structure.

One side of the head portion 30 may have an inclination angle of 24 to 26 degrees based on a bottom surface of the body portion 10, and the other side of the head portion 30 may have two-stage inclination angles based on the bottom surface of the body portion 10. The other side of the head portion 30 may have a first inclination section and a second inclination section, and the first inclination section may have a smaller inclination angle than the second inclination section.

As an exemplary embodiment, one side of the head portion 30 may have an inclination angle of 25 degrees, and at the other side of the head portion 30, the first inclination section may have an inclination angle of 15 to 16 degrees, and the second inclination section may have an inclination angle of 16 to 17 degrees. The reason is to bring the head portion 30 into close contact with the lower tibia 2b as the head portion 30 is twisted.

The other end of the body portion 10 may have two-stage inclination sections. The two-stage left and right inclination sections of the body portion 10 may have different inclination angles, and in the first inclination section and the second inclination section, the first inclination section may have a smaller inclination section than the second inclination section.

As an exemplary embodiment, the first inclination section at one side of the other end of the body portion 10 may have an inclination angle of 7.7 to 8.2 degrees, and the second inclination section may have an inclination angle of 14.5 to 15 degrees.

The first inclination section at the other side of the other end of the body portion 10 may have an inclination angle of 7.2 to 7.7 degrees, and the second inclination section may have an inclination angle of 16.8 to 17.3 degrees. The reason is to bring the body portion 10 into close contact with the upper tibia 2a as the body portion 10 is twisted.

Figure 6:
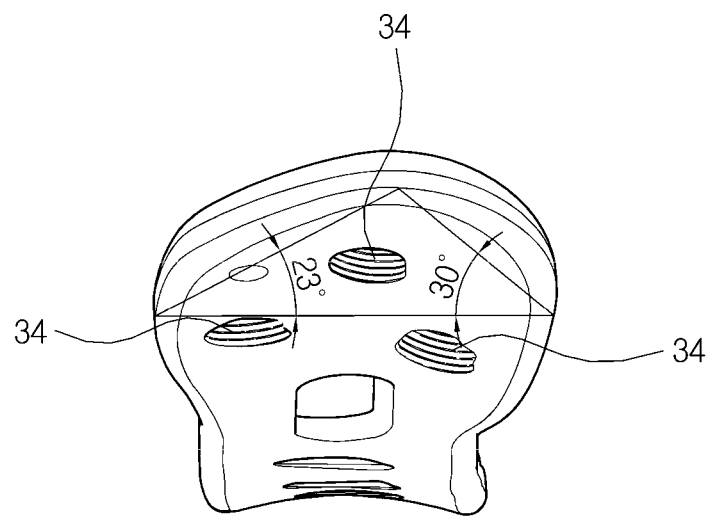
FIG. 6 is a view illustrating the plate in FIG. 3 when viewed from a head portion.

FIG. 6 is a view illustrating the plate, which is a constituent element of the present invention, when viewed from the head portion.

Referring to FIG. 6, the plate 100 may be formed to be curved so as to have a predetermined curvature so that the plate 100 may be in close contact with an outer circumferential surface of the tibia 2. There is no limitation on the curvature of the plate 100, and the curvature of the plate 100 may be variously modified.

The head portion 30 may be provided such that lines, which connect a single uppermost point and left and right outermost points, form a triangle. The uppermost point may be slanted toward one side as the head portion 30 is twisted. As an exemplary embodiment, among angles which are formed when connecting left and right outermost points of the triangle formed on the head portion 30, one inclination angle may be 29 to 31 degrees, and the other inclination angle may be 22 to 24 degrees.

Since the twisted plate 100 may be in close contact with the tibia 2 as described above, it is possible to improve supporting force of the plate 100.

Figure 7:
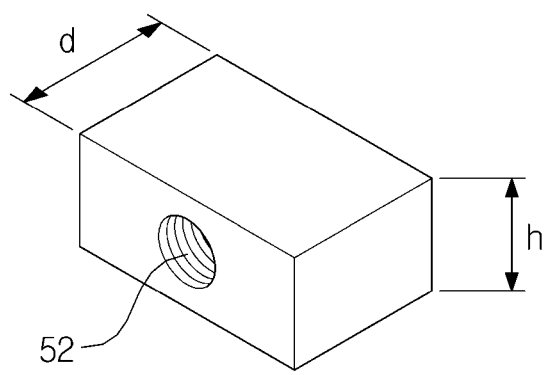
FIG. 7 is a view illustrating a shape of a block which is a constituent element of the present invention.

FIG. 7 is a view illustrating a shape of the block which is a constituent element of the present invention.

Referring to FIG. 7, the block 50 may be inserted into the incised portion 3, and may support the upper tibia 2a and the lower tibia 2b. The block 50 may have a quadrangular column shape, a through hole 52 may be formed in a longitudinal direction d, and the sliding screw 54 may penetrate the oblong hole 20 and then may be coupled to the through hole 52. A material of the block 50 may be modified to various materials such as metal or reinforced plastic.

As an exemplary embodiment, a length d of the block 50 may be 4 to 10 mm, particularly, 8 mm.

A height h of the block 50 may be any one of 3.8 to 4.2 mm, 5.8 to 6.2 mm, 7.8 to 8.2 mm, and 9.8 to 10.2 mm, and the height h of the block 50 may be variously modified in accordance with a width of the incised portion 3.

The shape of the block 50 is just an example, and may be modified to various shapes to be inserted into the incised portion 3.

As described above, according to the fixing instrument for an open-type distal tibial osteotomy according to the exemplary embodiment of the present invention, it is possible to securely couple the plate and the bone by rotating the head portion.

In addition, since angles are formed at the head portion and thus the coupling screws are not withdrawn from the bone, it is possible to reduce complications after the surgery.

In addition, the sliding hole is formed in the body portion, such that the block may be inserted to be suitable for a surgical site.

The above description is simply given for illustratively describing the technical spirit of the present invention, and those skilled in the art to which the present invention pertains will appreciate that various modifications, changes and substitutions are possible without departing from the essential characteristic of the present invention. Accordingly, the exemplary embodiment disclosed in the present invention and the accompanying drawings are intended to not limit but describe the technical spirit of the present invention, and the scope of the technical spirit of the present invention is not limited by the exemplary embodiment and the accompanying drawings. The protective scope of the present invention should be construed based on the following claims, and all the technical spirit in the equivalent scope thereto should be construed as falling within the scope of the present invention.

The invention claimed is:

1. A fixing instrument for an open-type distal tibial osteotomy which is configured to be installed on an upper tibia and a lower tibia incised by the open-type distal tibial osteotomy, the fixing instrument comprising:
    a body portion comprising coupling body holes and an oblong hole, wherein the body portion has a top body end, a bottom body end opposite to the top body end along a longitudinal direction, an upper body surface, and a lower body surface opposite to the upper body surface along a vertical direction to the longitudinal direction; and wherein the lower body surface is configured to directly contact the upper tibia;
    a head portion comprising coupling head holes, wherein the head portion has an upper head surface and a lower head surface opposite to the upper head surface; and wherein the head portion directly contacts the top body end and the lower head surface is configured to directly contact the lower tibia;
    coupling body screws inserted into the coupling body holes;
    coupling head screws inserted into the coupling head screws; and
    a block detachably installed in the oblong hole by using a sliding screw,
    wherein the head portion is formed to have a predetermined angle based on the lower body surface,
    wherein the head portion is formed to asymmetrically tilt in a left or right direction with respect to the longitudinal direction, and
    wherein the bottom body end has two-stage body inclination sections having different inclination angles from each other along the longitudinal direction.

2. The fixing instrument of claim 1, wherein the head portion is formed to be wider in width than the body portion, and the coupling head holes are formed such that centers of the coupling head holes are positioned at apices of a triangle.

3. The fixing instrument of claim 1, wherein the head portion and the body portion are curved.

4. The fixing instrument of claim 3, wherein the lower head surface has an inclination angle of 24 to 26 degrees based on the lower body surface.

5. The fixing instrument of claim 1, wherein the lower head surface has two-stage head inclination sections based on the lower body surface.

6. The fixing instrument of claim 5, wherein the two-stage head inclination sections include a first head inclination portion and a second head inclination portion, and the first head inclination portion has a smaller inclination angle than the second head inclination portion.

7. The fixing instrument of claim 6, wherein the first head inclination portion forms an inclination angle of 15 to 16 degrees based on the lower body surface, and the second head inclination portion forms an inclination angle of 16 to 17 degrees based on the lower body surface.

8. The fixing instrument of claim 1, wherein the two-stage body inclination sections have a first body inclination section and a second body inclination section in order toward the bottom body end, and the first body inclination section has a smaller inclination angle than the second body inclination section.

9. The fixing instrument of claim 1, wherein at least one guide hole to which a guide pin is fixed is formed in the head portion or the body portion.

10. The fixing instrument of claim 1, wherein a length of the block configured to be inserted into an incised portion is 4 to 10 mm, and a height thereof is one range of 3.8 to 4.2 mm, 5.8 to 6.2 mm, 7.8 to 8.2 mm, and 9.8 to 10.2 mm.

* * * * *